(12) United States Patent
Umeda

(10) Patent No.: US 6,349,127 B1
(45) Date of Patent: Feb. 19, 2002

(54) PULLEY AND CT SCANNER

(75) Inventor: Hiroshi Umeda, Tokyo (JP)

(73) Assignee: GE Yokogawa Medical Systems, Limited, Tokyo (JP)

( * ) Notice: Subject to any disclaimer, the term of this patent is extended or adjusted under 35 U.S.C. 154(b) by 0 days.

(21) Appl. No.: 09/157,355

(22) Filed: Sep. 19, 1998

(30) Foreign Application Priority Data

Sep. 26, 1997 (JP) ............................................. 9-261286

(51) Int. Cl.[7] ................................................. A61B 6/03
(52) U.S. Cl. .......................... 378/15; 434/157; 434/152; 434/164
(58) Field of Search .................. 474/157, 152, 474/164; 378/4, 15, 19

(56) References Cited

U.S. PATENT DOCUMENTS 3,225,616 A 12/1965 Whitehead
3,891,868 A * 6/1975 Joyce .......................... 474/152
4,115,695 A 9/1978 Kelman
5,982,844 A * 11/1999 Tybinkowski et al. ......... 378/4

FOREIGN PATENT DOCUMENTS

JP 8-024249 1/1996

* cited by examiner

Primary Examiner—David P. Porta
(74) Attorney, Agent, or Firm—Moonray Kojima

(57) ABSTRACT

With a view of facilitating the manufacture and reducing the cost, a pulley according to the present invention comprises an annular portion 100 formed by laminating rings 110, 120 and 130 and a tooth portion formed along a circumferential surface of the annular portion 100, the tooth portion comprising a plurality of resin teeth having blades formed on the side opposite to the side which is opposed to the circumferential surface of the annular portion. The rings 110, 120 and 130 are divided into a plurality of arcuate plates 111, 112, 113, 121, 122, 123, 131, 132 and 133.

6 Claims, 6 Drawing Sheets

PULLEY AND CT SCANNER

BACKGROUND OF THE INVENTION

The present invention relates to a pulley (belt pulley) and a CT (Computed Tomography) scanner using the pulley.

As a pulley of a large diameter such as a driven pulley used in a CT scanner there generally is used a cast aluminum pulley.

Such a cast pulley is manufactured by forming an annular member by casting and then forming teeth on a circumferential surface of the annular member with use of a machine tool such as, for example, a face lathe.

However, the above cast pulley involves the problem that machining such as lathing requires much time and labor.

There is another problem of an increase in cost because it is necessary to fabricate a mold for casting.

SUMMARY OF THE INVENTION

It is an object of the present invention to provide a pulley easy to manufacture and capable of being reduced its cost.

It is another object of the present invention to provide a CT scanner using a pulley which is easy to manufacture and whose cost can be reduced.

According to the present invention, for solving the foregoing problems, there is provided in the first aspect thereof a pulley comprising an annular portion formed by laminating generally annular plates, and a tooth portion formed along a circumferential surface of the annular portion, the tooth portion comprising a plurality of resin teeth having blades formed on the side opposite to the side which is opposed to the circumferential surface of the annular portion, the generally annular plates of the annular portion being each divided into a plurality of arcuate plates.

Since the pulley is constituted by an annular portion formed by laminating generally annular plates and a tooth portion comprising a plurality of resin teeth formed on a circumferential surface of the annular portion, the pulley can be manufactured easily at a reduced cost.

Moreover, the rigidity of the pulley can be enhanced easily by increasing the number of generally annular plates laminated.

The cost of the pulley can be further reduced because the generally annular plates are each constituted by arcuate plates which are easy for blanking.

A still further reduction of the cost can be attained because the tooth portion is constituted by a plurality of resin teeth.

In the second aspect of the present invention there is provided, in combination with the pulley in the first aspect, a pulley wherein the generally annular plate of each layer is divided in positions different from divided positions of the generally annular plate of a layer adjacent thereto.

Thus, the divided positions of the generally annular plates of the constituent layers are shifted from one another, whereby the deterioration of rigidity can be made smaller than the case where the divided positions are aligned.

In the third aspect of the present invention there is provided, in combination with the pulley in the first or the second aspect, a pulley wherein a component to be attached to a side face of the annular portion is mounted so as to straddle the arcuate plates adjacent to each other.

By mounting a component so as to straddle adjacent arcuate plates, the rigidity of the pulley is improved.

In the fourth aspect of the present invention there is provided a CT scanner comprising a rotatable frame mounted rotatably with respect to a fixed frame, a driven pulley mounted on the rotatable frame, a driving pulley mounted rotatably on the fixed frame and rotated by means of a drive source, and a belt wound between the driven pulley and the driving pulley, the driven pulley including an annular portion formed by laminating generally annular plates and a tooth portion formed along a circumferential surface of the annular portion, the tooth portion comprising a plurality of resin teeth having blades formed on the side opposite to the side which is opposed to the circumferential surface of the annular portion, the generally annular plates of the annular portion being each divided into a plurality of arcuate plates.

Since the driven pulley is constituted by an annular portion formed by laminating generally annular plates and a tooth portion comprising a plurality of resin teeth formed on a circumferential surface of the annular portion, the driven pulley can be manufactured easily at a reduced cost.

Moreover, by increasing the number of generally annular plates laminated, the rigidity of the pulley can be enhanced easily.

Further, since the generally annular plates are each constituted by arcuate plates which are easy for blanking, there can be attained a further reduction of cost.

It is possible to attain a still further reduction of cost because the tooth portion is constituted by a plurality of resin teeth.

As set forth above, according to the pulley in the first aspect of the present invention, there can be attained both easy manufacture and reduction of cost because the pulley is constituted by an annular portion formed by laminating generally annular plates and a tooth portion comprising a plurality of resin teeth formed on a circumferential surface of the annular portion.

Moreover, the rigidity can be enhanced easily by increasing the number of generally annular plates laminated.

A further reduction of cost can be attained since the generally annular plates are each constituted by arcuate plates which are easy for blanking.

Further, the formation of plural resin teeth to constitute the tooth portion can also contribute to the reduction of cost.

According to the pulley in the second aspect of the present invention, since the divided positions of the generally annular plates as constituent layers of the annular portion are shifted from one another, it is possible to keep low the deterioration of rigidity in comparison with the case where the divided positions are aligned.

According to the pulley in the third aspect of the present invention, the rigidity of the pulley is improved because a component is mounted so as to straddle arcuate plates adjacent to each other.

According to the CT scanner in the fourth aspect of the present invention, since the driven pulley used therein is constituted by an annular portion formed by laminating generally annular plates and a tooth portion comprising a plurality of resin teeth formed on a circumferential surface of the annular portion, the manufacture is easy and the cost can be reduced.

Besides, the rigidity can be enhanced easily by increasing the number of generally annular plates laminated.

A further reduction of cost can be attained because the generally annular plates are each constituted by arcuate plates which are easy for blanking.

Further, since the tooth portion is constituted by a plurality of resin teeth, the reduction of cost can also be attained.

Further objects and advantages of the present invention will become apparent from the following description of the preferred embodiments of the invention as illustrated in the accompanying drawings.

DETAILED DESCRIPTION OF THE INVENTION

Embodiments of the present invention will be described hereinafter with reference to the accompanying drawings.

Figure 5:
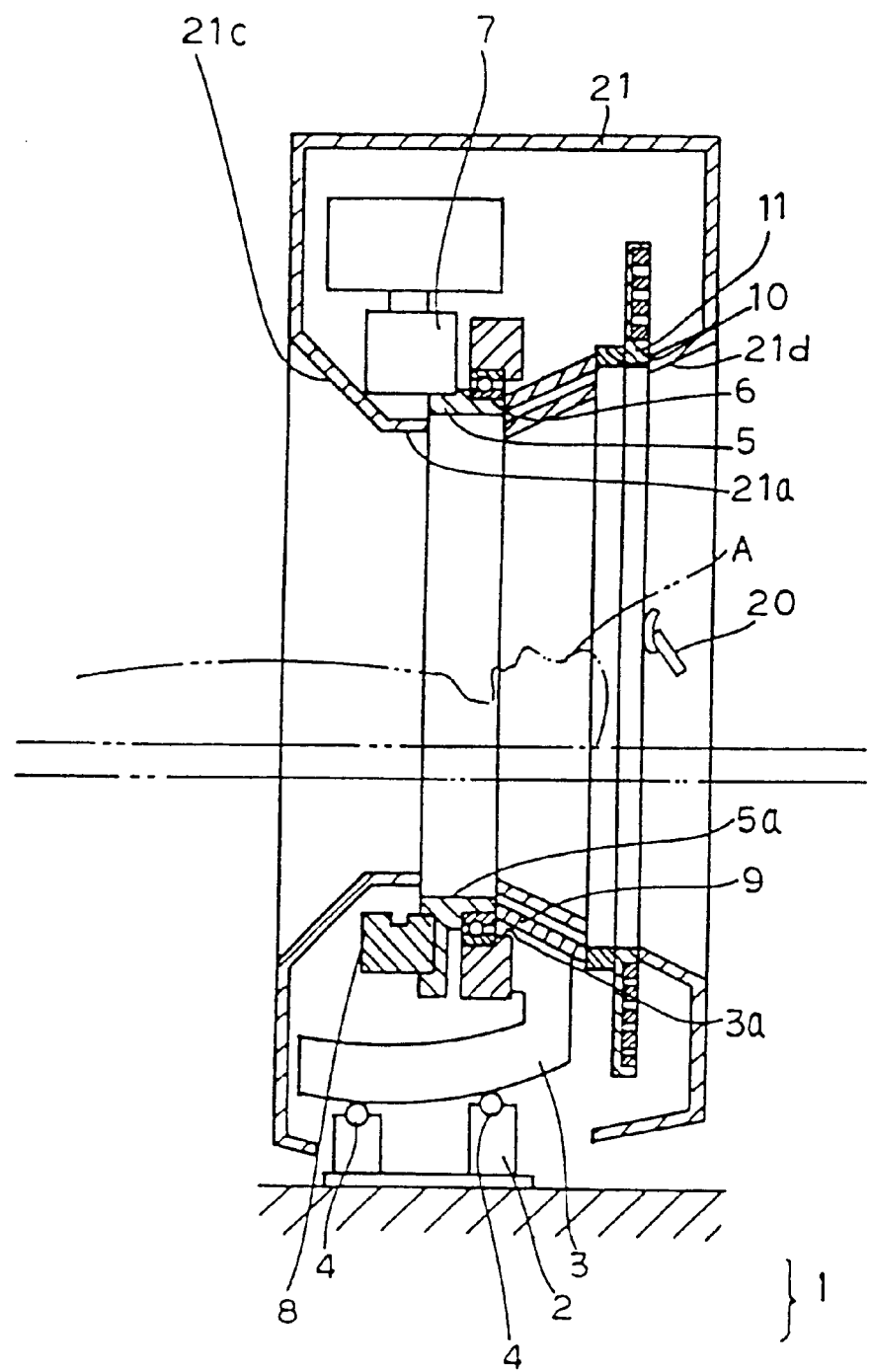
FIG. 5 is a sectional side view of a gantry used in a CT scanner.
Figure 6:
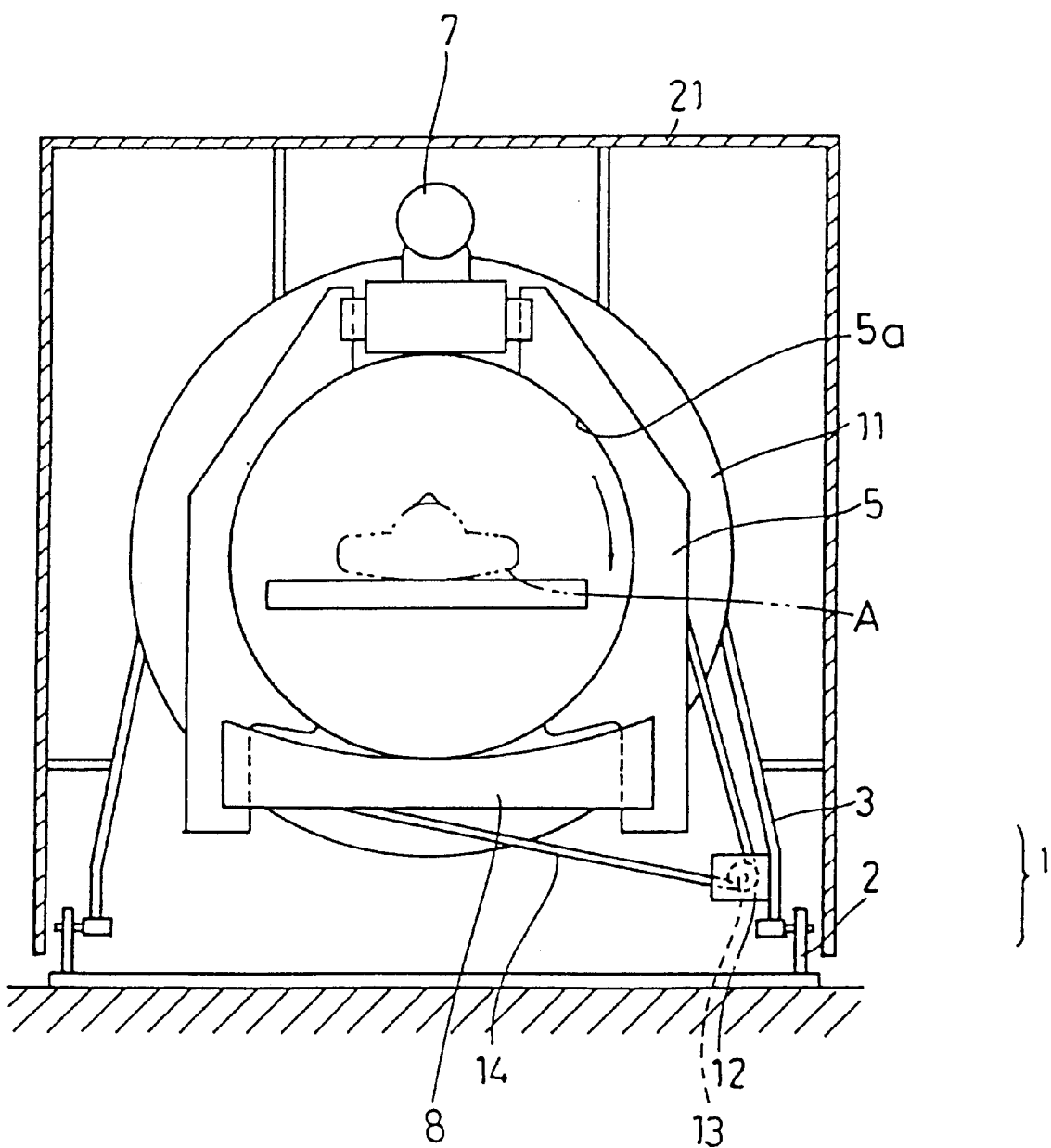
FIG. 6 is a sectional front view thereof.

First, an entire construction of a CT scanner provided with a pulley according to an embodiment of the present invention will be described with reference to FIGS. 5 and 6. FIG. 5 is a sectional side view of a gantry used in the CT scanner and FIG. 6 is a sectional front view thereof.

In both figures, the numeral 1 denotes a fixed frame provided on a floor side. The fixed frame 1 substantially comprises a lower frame 2 and an upper frame 3 having an opening 3a for a subject. An underside of the upper frame 3 is formed as a downwardly convex arcuate surface and is capable of rocking longitudinally with respect to the lower frame 2 through rollers 4.

Numeral 5 denotes a rotatable frame having an opening 5a for a subject and which is rotatable with respect to the upper frame 3 of the fixed frame 1 through a bearing 6.

On the rotatable frame 5 are mounted a radiation source 7 for emitting radiation to a subject and a detector 8 for detecting the radiation which has passed through the subject.

An annular driven pulley 10 is also mounted on the rotatable frame 5 through an extension stage 9. An annular slip ring plate 11 to which a plurality of electrically conductive rings of different diameters are mounted concentrically is disposed adjacent the driven pulley 10 in an approximately horizontal direction.

On the other hand, a drive source 12 is provided on the fixed frame 1 side and a driving pulley 13 is mounted on an output shaft of the drive source 12, with a belt 14 being wound between and the driven pulley 10 and the driving pulley 13.

Also, on the fixed frame 1 side is mounted a brush 20 which is in sliding contact with the slip ring plate 11 to supply an electric current to and transmit and receive signals to and from the radiation source 7 and the detector 8 both provided on the rotatable frame 5 side.

The numeral 21 denotes a cover which covers the above components. The cover 21 has an opening 21a. As the opening 21a approaches open end faces, it forms conical faces 21b and 21c which are larger in diameter outwards to diminish a sense of oppression of the subject A lying in the opening 21a.

The operation of the CT scanner constructed as above will now be described. Upon operation of the drive source 12, the driven pulley 10 mounted on the rotatable frame 5 side is rotated through the driving pulley 13 and the belt 14.

Then, the radiation emitted from the radiation source 7 passes through the subject A lying in the opening 21a and is detected by the detector 8.

Figure 1:
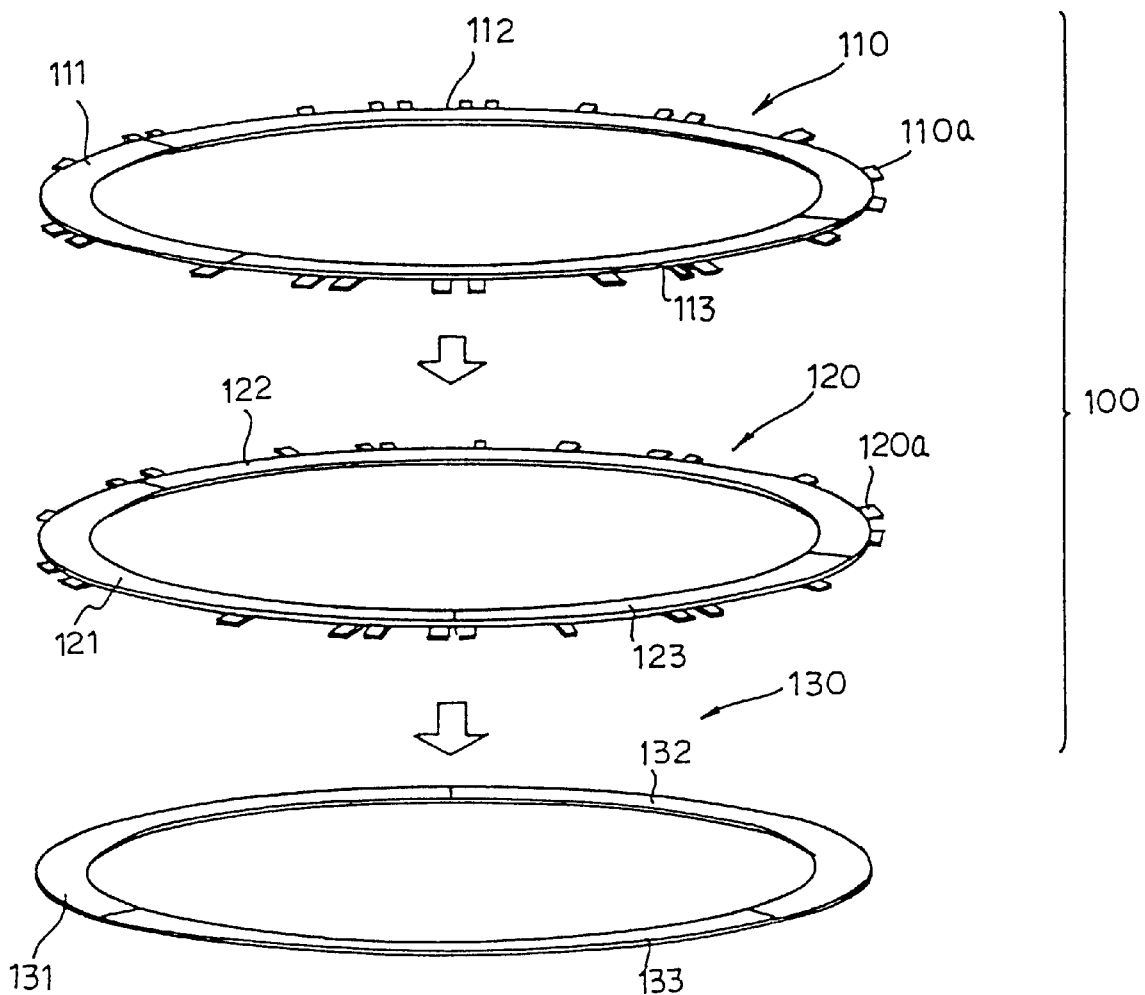
FIG. 1 is an exploded perspective view of an annular portion of a driven pulley.

Now, with reference to FIGS. 1 to 3, a description will be given of the driven pulley 10 embodying the present invention. FIG. 1 is an exploded perspective view of an annular portion of the driven pulley shown in FIG. 1, FIG. 2 is a construction diagram of a tooth portion formed on a circumferential surface of the annular portion shown in FIG. 1, and FIG. 3 is a diagram illustrating in what manner the tooth portion of the driven pulley shown in FIG. 1 is mounted and in what manner the driven pulley is mounted with respect to an extension stage and a slip ring plate.

Figure 2:
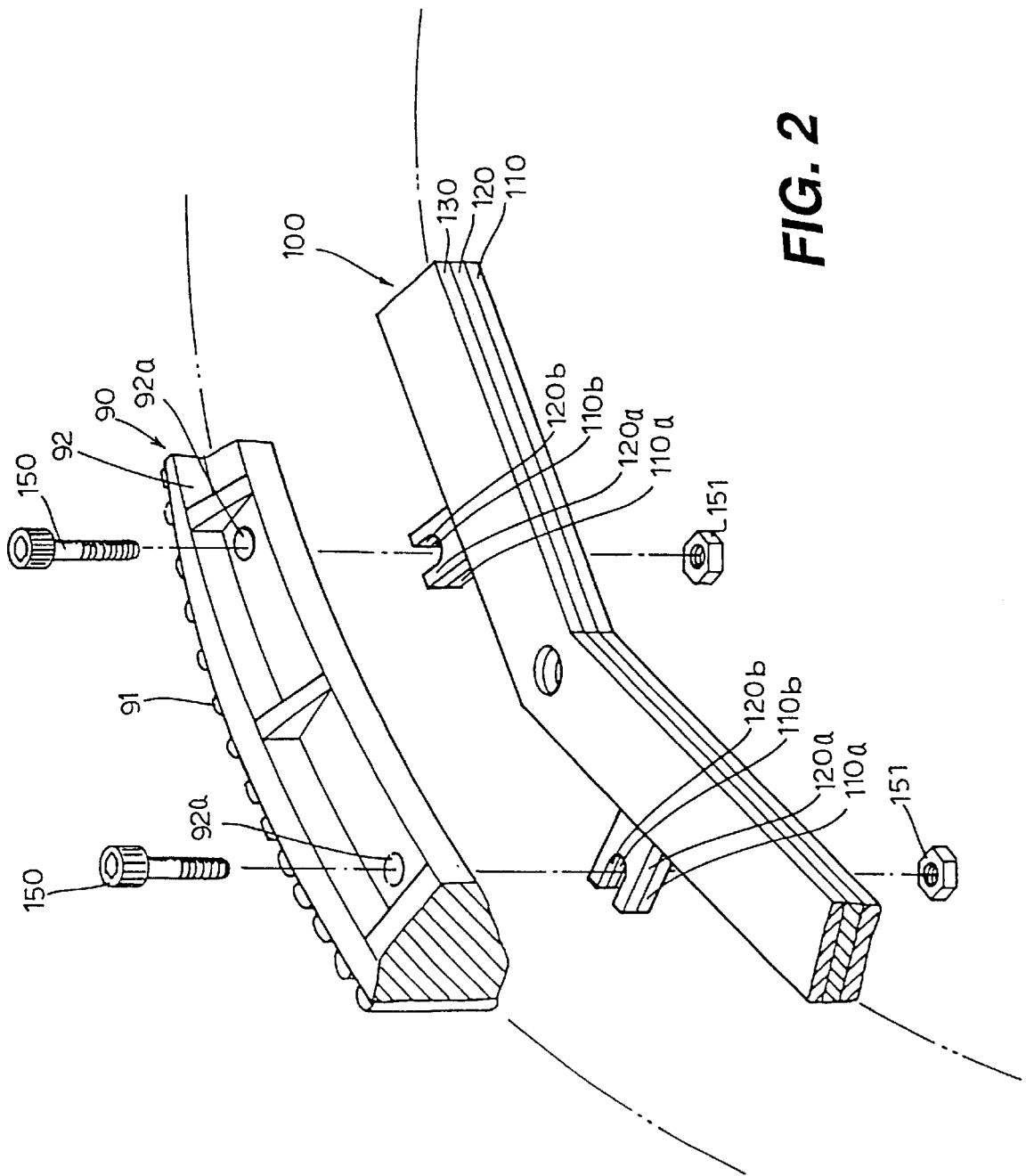
FIG. 2 is a construction diagram of a tooth portion mounted on a circumferential surface of the annular portion shown in FIG. 1.
Figure 3:
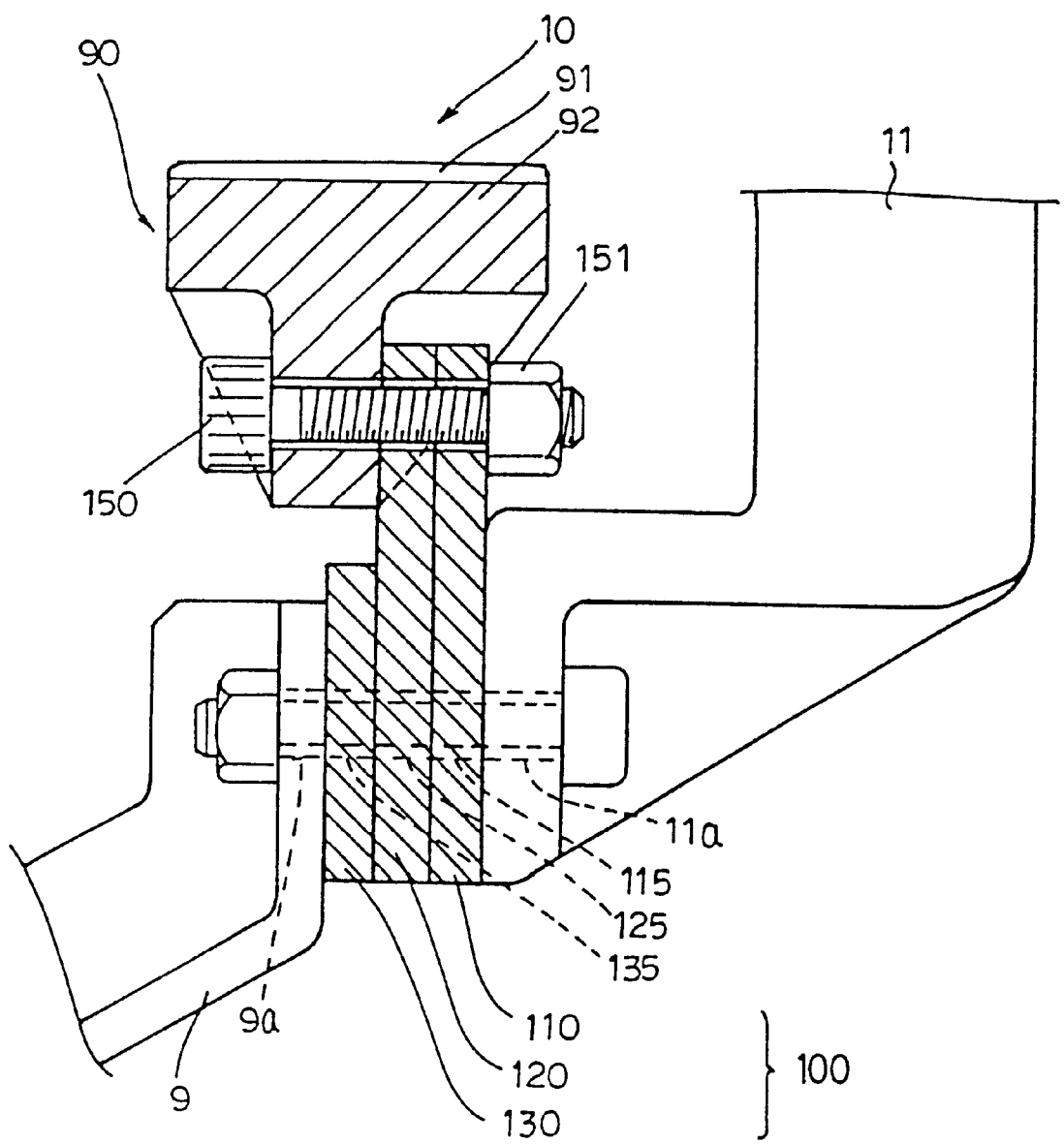
FIG. 3 is a diagram illustrating in what manner the tooth portion of the driven pulley shown in FIG. 1 is mounted and in what manner the driven pulley is mounted with respect to an extension stage and a slip ring plate.

As shown in FIG. 2, the driven pulley 10 comprises an annular portion 100 and a tooth portion 90 formed along a circumferential surface of the annular portion 100, the tooth portion 90 comprising a plurality of resin teeth 92 having blades 91 formed on the side opposite to the side which is opposed to the circumferential surface of the annular portion 100.

As shown in FIG. 1, the annular portion 100 comprises three generally annular plates which are a first ring 110, a second ring 120 and a third ring 130.

The first ring 110 is divided into three arcuate plates 111, 112 and 113. Likewise, the second and third rings 120, 130 are also divided into three arcuate plates 121, 122, 123 and three arcuate plates 131, 132, 133, respectively.

The first, second and third rings 110, 120, 130 are laminated together in such a manner that the divided positions of the arcuate plates 111, 112, 113 of the first ring 110, the divided positions of the arcuate plates 121, 122, 123 of the second ring 120, and the divided positions of the arcuate plates 131, 132, 133 of the third ring 130, are different from one another. The three rings thus laminated are then clamped together using rivets or the like to constitute the annular portion 100.

Further, a plurality of bracket portions 110a and 120a for mounting the resin teeth 92 are formed on circumferential surfaces of the first and second rings 110, 120, respectively. The bracket portions 110a and 120a are formed so as to be aligned with each other when both rings are laminated together.

In this embodiment, the rings 110, 120 and 130 are each formed in a polygonal shape closely similar to a circular arc so that they can be obtained using a turret punch.

The resin teeth 92 is mounted to a circumferential surface of the annular portion 100, using bolts 150 and nuts 151 threadedly engaged with the bolts 150, the bolts 150 being inserted into holes 92a formed in the resin teeth 92 and further through U-shaped slots 120b, 110b formed in the bracket portions 120a, 110a, respectively.

As shown in FIG. 3, the driven pulley 10, the slip ring plate 11 and the extension stage 9 are mounted by being clamped together with bolts 160 and nuts 161 which are threaded engaged with the bolts 160, the bolts 160 each being inserted into a through hole 11a, through holes 115, 125 and 135 formed in the rings 110, 120 and 130, respectively, and a through hole 9a formed in the extension stage 9.

Figure 4:
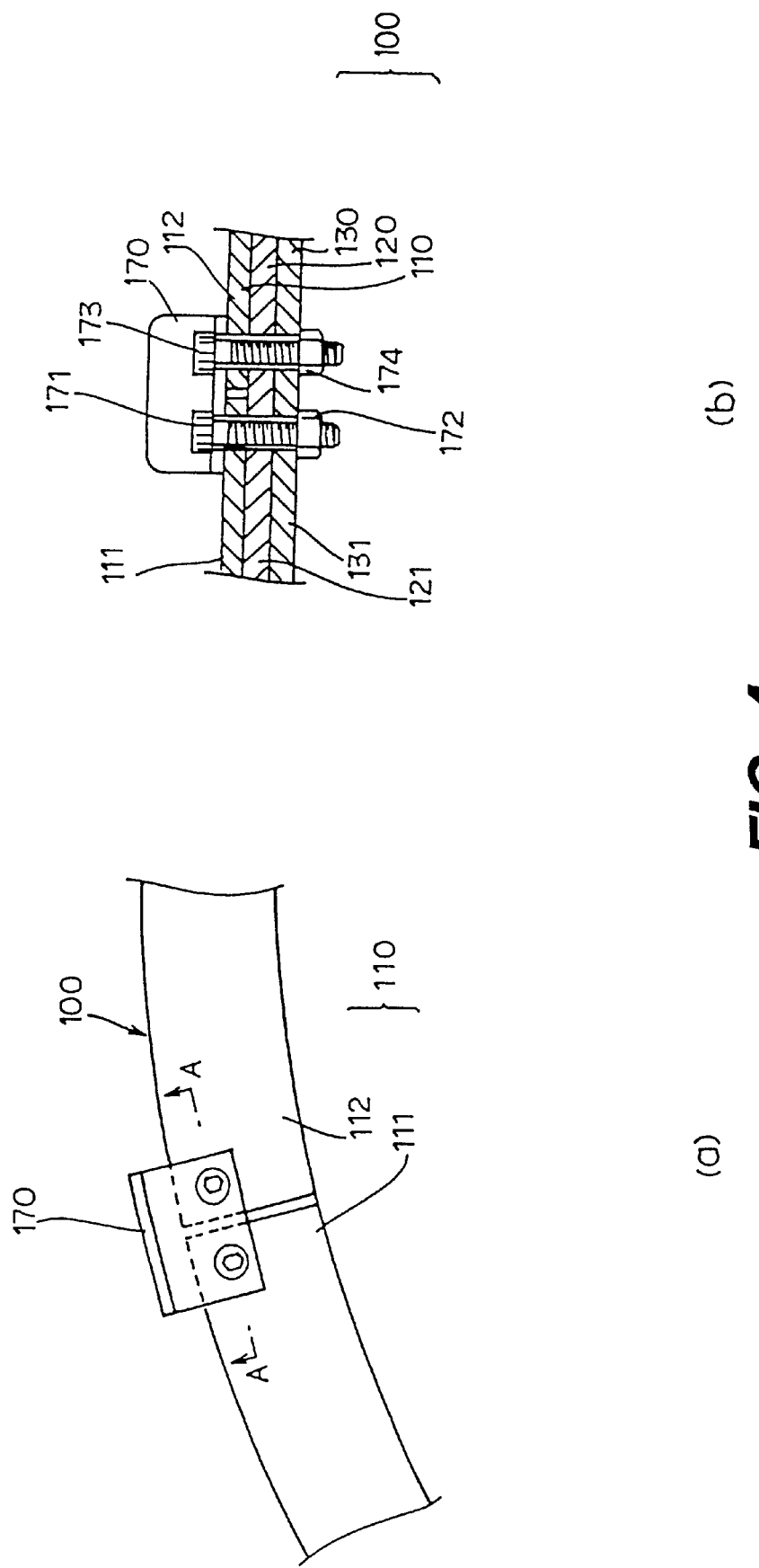
FIGS. 4(a) and 4(b) are diagrams illustrating in what manner a component, if any, is to be attached to a side face of the annular portion, in which 4(a) is a front view and 4(b) is a sectional view taken on line A—A in (a)

As shown in FIG. 4, if there is a component 170 to be attached to a side face of the annular portion 100, the component 170 is mounted so as to straddle arcuate plates 111 and 112 adjacent to each other, and out of two sets of bolts and nuts for mounting the component 170 to the annular portion 100, one set of bolt 171 and nut 172 are used to clamping the plates 111, 121 and 131 together, while the other set of bolt 173 and nut 174 are used to clamping the plates 112, 121 and 131 together.

According to the driven pulley 10 of the above construction, there can be obtained the following effects. (1) Since the driven pulley 10 is composed of the annular portion 100 formed by laminating the rings 110, 120 and 130 and the tooth portion 90 which comprises a plurality of resin teeth 92 formed on a circumferential surface of the annular portion, the driven pulley can be manufactured easily at a reduced cost. (2) The rigidity of the driven pulley 10 can be enhanced easily by increasing the number of rings laminated. (3) Since the rings 110, 120 and 130 are constituted by arcuate plates 111, 112, 113, 121, 122, 123, 131, 132 and 133 which are easy for blanking, it is possible to attain a further reduction of cost. (4) The reduction of cost can also be attained since the tooth portion 90 is constituted by a plurality of resin teeth 92. (5) Since the divided positions of the rings 110, 120 and 130 in the annular portion are deviated from one another, the deterioration of rigidity can be kept smaller than the case where the divided positions are aligned with one another. (6) By mounting the component 170 so as to straddle the arcuate plates 111 and 112 which are adjacent to each other, the rigidity of the driven pulley 10 is improved.

The present invention is not limited to the above embodiments. Although in the above embodiments each ring is divided into three plates, it is desirable to change the number of divisions in accordance with the diameter of the driven pulley and the size of the material to be subjected to turret punching.

Many widely different embodiments of the invention may be constructed without departing from the spirit and the scope of the present invention. It should be understood that the present invention is not limited to the specific embodiments described in the specification, except as defined in the appended claims.

What is claimed is:

1. A pulley comprising:
    an annular portion formed by laminating together in successive layers a plurality of annular plates; and
    a separate tooth portion disposed along a circumference of the annular portion and connected thereto,
        the tooth portion being of resin material and comprising a plurality of teeth formed on an outside circumference thereof, and
        the annular plates being each divided into a plurality of arcuate sections.

2. The pulley of claim 1 wherein the annular plate of each layer is divided in positions different from divided positions of the annular plate of a layer adjacent thereto.

3. A CT scanner comprising:
    a rotatable frame mounted rotatably with respect to a fixed frame;
    a driven pulley mounted on the rotatable frame;
    a driving pulley mounted rotatably on the fixed frame and rotated by means of a drive source; and
    a belt wound between the driven pulley and the driving pulley, the driven pulley including an annular portion formed by laminating annular plates and a tooth portion formed along the annular portion, the tooth portion comprising a plurality of teeth having blades formed on the outside, the annular plates of the annular portion being each divided into a plurality of arcuate plates, and further comprising a component to be attached to a side face of the annular portion mounted so as to straddle the arcuate plates adjacent to each other.

4. The CT scanner of claim 3, wherein the annular plates are disposed in layers, each plate of each layer being divided in positions different from divided positions of the annular plate of a layer adjacent thereto.

5. A pulley comprising:
    an annular portion formed by laminating annular plates, and
    a tooth portion formed along the annular portion, the tooth portion comprising a plurality of teeth having blades formed on the outside, the annular plates of the annular portion being each divided into a plurality of arcuate plates; wherein
        a component to be attached to a side face of the annular portion is mounted so as to straddle the arcuate plates adjacent to each other.

6. The pulley of claim 5, wherein the annular plates are disposed in layers, each plate of each layer being divided in positions different from divided positions of the annular plate of a layer adjacent thereto.

* * * * *